United States Patent [19]
Buitar et al.

[11] 3,931,161
[45] Jan. 6, 1976

[54] CEPHALOSPORIN DERIVATIVES

[75] Inventors: Carlo Buitar, Bologna; Giuseppe Mascellani, San Pietro, Bologna; Guido Guerra, Bologna, all of Italy

[73] Assignee: Alfa Farmaceutici S.p.A., Bologna, Italy

[22] Filed: Mar. 6, 1973

[21] Appl. No.: 338,515

[30] Foreign Application Priority Data
Mar. 9, 1972 United Kingdom............... 11006/72

[52] U.S. Cl............................. 260/243 C; 424/246
[51] Int. Cl.² ........................................ C07D 501/20
[58] Field of Search ................................ 260/243 C

[56] References Cited
UNITED STATES PATENTS

| | | | |
|---|---|---|---|
| 3,573,295 | 3/1971 | Johnson et al. | 260/243 C |
| 3,573,296 | 3/1971 | Johnson et al. | 260/243 C |
| 3,575,970 | 4/1971 | Weissenburger et al. | 260/243 C |
| 3,641,018 | 2/1972 | Hayes et al. | 260/243 C |
| 3,813,389 | 5/1974 | Hayes. | 260/243 C |
| 3,821,208 | 6/1974 | Stables et al. | 260/243 C |

Primary Examiner—Nicholas S. Rizzo
Attorney, Agent, or Firm—Ostrolenk, Faber, Gerb & Soffen

[57] ABSTRACT

Novel cephalosporin derivatives, for example N-acetoacetylcephalosporin C, N-decanoylcephalosporin C, N-dodecanoylcephalosporin C and N-hendecenoylcephalosporin C, are useful as readily-recoverable intermediates in the isolation of cephalosporin C value from fermentation broths and in the preparation of 7-aminocephalosporanic acid. They are prepared by treating an aqueous solution containing cephalosporin C, such as a fermentation broth, with diketene or an acid chloride such as decanoyl chloride, dodecanoyl chloride or hendecenoyl chloride, followed by solvent extraction. They are converted into 7-aminocephalosporanic acid by successively forming the silyl di-ester, halogenating to the iminohalide, converting the imino-ether and hydrolysing to 7-ACA.

11 Claims, No Drawings

CEPHALOSPORIN DERIVATIVES

BACKGROUND OF THE INVENTION

This invention relates to novel cephalosporin derivatives, which are useful intermediates in the isolation of cephalosporin C from fermentation broths and in the preparation of 7-aminocephalosporanic acid, to a process for the preparation of the said derivatives from fermentation broths containing cephalosporin C, and to their subsequent conversion into 7-aminocephalosporanic acid.

7-Aminocephalosporanic acid (hereinafter referred to as 7-ACA), which has the formula:

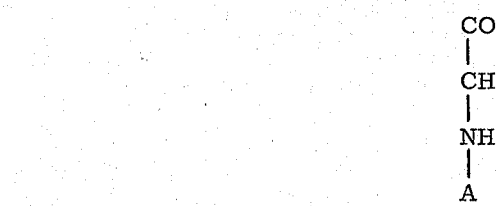

is useful as an intermediate in the preparation of many semi-synthetic cephalosporanic acid antibacterial agents. Most 7-ACA is produced from cephalosporin C, which has the formula:

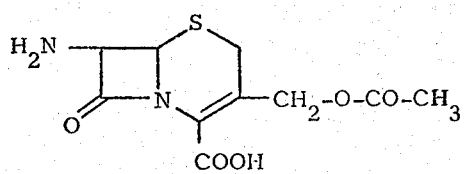

either by chemical degradation (e.g. as described in U.S. Pat. Nos. 3,124,576, 3,188,311 and 3,234,223) or by enzymatic hydrolysis of the side-chain (e.g. as described in French Pat. No. 1,357,977).

Cephalosporin C is produced by fermentation. However, its highly polar nature renders it very soluble in water, and it is very difficult to recover it from the fermentation broth by solvent extraction. The recovery precedure most generally used at present involves the adsorption of the crude cephalosporin C from the fermentation broth onto a suitable adsorbant, for example, charcoal or an ion exchange resin, followed by elution, concentration and precipitation at the isoelectric point, or by salt formation (see, for example, U.S. Pat. No. 3,094,527). The complexity of this multi-step process, and the low yields obtained thereby, render it unfavourable for the production of cephalosporin C and hence of 7-ACA.

SUMMARY OF THE INVENTION

It is an object of the present invention to provide a simplified and more efficient process for recovering cephalosporin C value from fermentation broths.

It is another object of the invention to provide a class of new cephalosporin C derivatives which can be used to increase the harvestable yields of cephalosporin C from fermentation broths, in a form directly usable for the production of 7-ACA, without complex purification procedures.

It is a further object of the invention to provide a process for preparing novel cephalosporin derivatives from an aqueous solution containing cephalosporin C.

It is a still further object of the invention to provide a new process of preparing 7-ACA which makes use of said novel cephalosporin derivatives.

In accordance with the foregoing objects, the invention provides cephalosporin derivatives of formula:

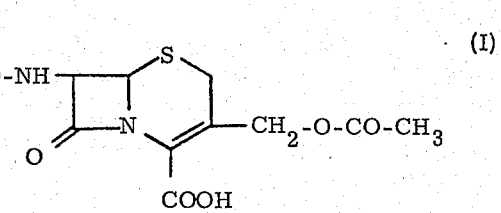

(wherein A represents the group $CH_3COCH_2CO-$ or $R-CO-$; and R is a straight or branched, saturated or unsaturated aliphatic hydrocarbyl group having from 9 to 21 carbon atoms) and salts and esters thereof.

The compounds of the invention can be prepared by a process which comprises reacting cephalosporin C with diketene or with an acid chloride of formula:

$$R-CO-Cl \quad (II)$$

(wherein R has the meaning already given) followed, if appropriate, by salification or esterification of the reaction product. In formula (I), A is preferably the acetoacetyl group ($CH_3COCH_2CO-$), or a decanoyl, dodecanoyl or hendecenoyl group; and, correspondingly, in the process of the invention the cephalosporin C is preferably reacted with diketene, decanoyl chloride, dodecanoyl chloride or hendecenoyl chloride.

As applied to fermentation broths containing cephalosporin C, the process of the invention broadly comprises treating the fermentation broth with diketene or with an acid chloride of formula (II), to form the corresponding cephalosporin derivative of formula (I), and recovering this derivative from the broth by solvent extraction, in a form directly usable for the production of 7-ACA.

DESCRIPTION OF THE PREFERRED EMBODIMENTS OF THE INVENTION

The fermentation of Cephalosporium species to produce cephalosporin C generally also gives a minor amount of cephalosporin N. The latter compound is not acid stable. Accordingly, when using the compounds of the invention for the recovery of cephalosporin C from a fermentation broth, any cephalosporin N present in the broth can be destroyed by acidification, before reacting the cephalosporin C with the diketene or the acid chloride. This is conveniently effected by acidifying the broth to about pH 2 and then incubating it for 1 to 5 hours. The fermentation broth may be filtered before or after the acidification and incubation. If desired, the fermentation broth may be concentrated by any of the convention techniques, for example, vacuum concentration or adsorption onto a suitable adsorbant followed by elution, and purified by treatment with a solvent such as acetone to precipitate impurities.

The reaction between the cephalosporin C and the diketene or acid chloride is generally carried out at a pH from 7 to 9, preferably at about pH 8. If an acidified fermentation broth filtrate is used, the pH can be raised by the addition of an alkali, such as sodium hydroxide or potassium hydroxide. The cephalosporin C solution can be mixed with from 15 percent to 100 percent of its own volume of a water-miscible inert organic solvent (i.e., one which does not react with the starting materials or with the products under the prevailing conditions), for example, acetone, tetrahydrofuran, dimethylformamide or dimethylacetamide. The diketene or acid chloride of formula (II) is gradually added to the solution with stirring, using at least 1.5 mole, and preferably from 2 to 15 moles, of this compound per mole of cephalosporin C. The pH of the solution is maintained at the stipulated value during this addition; and the temperature of the aqueous solution is maintained at from $-25°$ to $+50°C$, preferably at from $-10°$ to $+40°C$. The reaction is usually complete within 1-4 hours.

The compound of the invention, formed by reaction of the diketene or acid chloride with the free amino group of the cephalosporin C, can be recovered from the aqueous solution by extraction into a water-immiscible organic solvent at an acid pH. Typically, the reaction solution is extracted with about one-half of its own volume of a water-immiscible organic solvent, for example, methyl isobutyl ketone, butanol or butyl acetate, and the pH is lowered to 1 – 3. The mixture is agitated, and the organic phase containing the compound of the invention is collected. If a water-miscible organic solvent has been added during the previous stage, it is preferred, though not essential, to eliminate it from the reaction solution prior to this solvent extraction at an acid pH: this may be done by distilling it off under reduced pressure at a low temperature (e.g. at about 25°C), or by extraction with a water-immiscible organic solvent at a neutral pH, preferably using the same solvent as subsequently used for the extraction under acid conditions.

The organic solution of the compound of the invention thus obtained is then concentrated to about one-third to one-fifth of its original volume, at a temperature not exceeding 45°C. The concentrate is cooled to about 20°C, and the desired product can be isolated by one of the following techniques:

a. The sodium salt of the product is precipitated by the addition of a slight stoichiometric excess of sodium ethylhexanoate dissolved in methyl isobutyl ketone or butanol. The mixture is cooled to 0° – 5°C for 3 – 5 hours, and the solid sodium salt of the compound of formula (I) is filtered off. The salt is washed with cold methyl isobutyl ketone and then with ligroin. The porduct is dried at about 25°C under reduced pressure.

b. A salt is precipitated by the addition of an organic base, for example, quinoline, cyclohexylamine, 5-ethyl-2-methylpyridine, 2-picoline, 3-picoline, 4-picoline, N-ethylmorpholine, N-methylmorpholine, 2,6-lutidine, N,N-diethylcyclohexylamine, hexamethylenetetramine, N,N-diethylbenzylamine, or N,N-dibenzylethylenediamine.

c. The compound of formula (I) is re-extracted into water, at a slightly alkaline pH, and the aqueous solution is concentrated under reduced pressure until crystallization begins. Crystallization may be facilitated by the addition to the solution of 1 – 2 times its volume of a water-miscible alcohol or of acetone. The crystalline salt is filtered off, washed with cold acetone, and dried at about 25°C under reduced pressure.

d. In some cases the product may be obtained by direct crystallization from the solvent.

The salts and esters of the compounds of formula (I) can be prepared from the free acid, or vice-versa, by means of the conventional techniques. Of the compound of the invention, the silyl di-esters are especially valuable for the preparation of 7-ACA.

Accordingly, the invention also provides a convenient process for the preparation of 7-ACA, making use of the silyl di-esters of the compounds of formula (I). The silyl group protects the carboxyl group on the cephalosporin nucleus during the preparation of the 7-ACA. This process for preparing 7-ACA comprises:

a. Forming a silyl di-ester of a compound of formula (I);

b. Halogenating the silyl di-ester, to give the corresponding imino-halide;

c. Reacting the imino-halide with a lower aliphatic alcohol, to give the corresponding imino-ether; and d. Hydrolysing the imino-ether under acidic conditions, to give 7-ACA.

This process can be performed in the same reaction medium, without isolating the intermediate at the end of each stage, and is capable of giving yields of 50 – 90 percent, under both laboratory and commercial conditions.

Suitable silyl di-esters can be prepared by reacting a compound of formula (I), or a salt thereof, with at least two equivalents of a lower alkyl silazane or polysilazane, or of a silyl compound of the formula:

wherein $R^1$ represents an alkyl group having from 1 to 6 carbon atoms, or an aryl group;

$R^2$ and $R^3$ may be the same or different, and each represents a hydrogen atom, a halogen atom, an alkyl or haloalkyl group having from 1 to 6 carbon atoms, or an aryl group; and Y represents a halogen atom or a lower dialkylamino group;

under anhydrous conditions.

Suitable salts of the compounds of formula (I), for use in the preparation of the silyl di-esters, include those with metals such as potassium, sodium, calcium, zinc, ferrous iron, cadmium, copper and aluminium, as well as ammonium and amine salts, in particular salts with tertiary amines such as trimethylamine, triethylamine, N-methylmorpholine, pyridine, 1-ephenamine and N-alkylpiperidines. Examples of silyl compounds which may be used in step (a) include trimethylchlorosilane, hexamethyldisilazane, triethylchlorosilane, methyltrichlorosilane, dimethyldichlorosilane, triethylbromosilane, tripropylchlorosilane, bromomethyldimethylchlorosilane, methyldiethylchlorosilane, phenyldimethylchlorosilane, triphenylchlorosilane, N-ethyltriethylsilylamine, hexaethyldisilazane and triphenylsilylamine. Dimethyldichlorosilane and trimethylchlorosilane are preferred. The reaction is suitably carried out in an inert organic solvent such as methylene chloride, dichloroethane, chloroform, tetrachloroethane, nitromethane, diethyl ether, dioxane, tetrahydrofuran, benzene or toluene. When using a silyl compound of formula (III) wherein Y represents a halogen atom, the reaction should be performed in the presence of an acid binding agent, for example, triethylamine, N,N-dimethylaniline, quinoline, lutidine or pyridine.

In step (b), the silyl di-ester is reacted with a halogenating agent, for example, phosphorus pentachloride, phosphorus pentabromide, phosphorus trichloride, phosphorus tribromide, phosphorus oxychloride, phosphorus oxybromide, oxalyl chloride, a p-toluenesulphonyl halide, or phosgene. At least 2 moles of the halogenating agent are used per mole of the silyl di-ester. The reaction is carried out under anhydrous conditions, in an inert organic solvent and in the presence of an acid binding agent; the solvent and acid binding agent used may be the same as those used in step (a). The amount of acid binding agent used is preferably equivalent to the amount of hydrohalic acid formed during the reaction. The reaction to produce the imino-halide is carried out at a temperature below 0°C, and preferably at a temperature from −20° to −65°C.

In step (c), the imino-halide is converted to the corresponding imino-ether by reaction with a primary or secondary aliphatic alcohol containing from 1 to 8, and preferably from 1 to 4, carbon atoms - for example, methanol, ethanol, propanol, isopropanol, or butanol. The reaction is carried out in anhydrous solution, at a temperature below 0°C, and preferably at a temperature from −20°C to −80°C.

Finally, the imino bond of the imino-ether is split, to give 7-ACA. This reaction of step (d) is effected by mild hydrolysis with water at a pH below 2. In general, the reaction medium is already sufficiently acid for the hydrolysis to occur spontaneously. However, if an excess of acid binding agent has been used in the previous steps, the careful addition of a dilute mineral acid will be needed to effect this hydrolysis.

The 7-ACA thus produced can be recovered from solution by adjusting the pH to around its isoelectric point (pH 3.2 – 3.4), so that it crystallizes out and can then be filtered off. The process is capable of yielding 7-ACA with a purity greater than 90 percent, which may be employed directly for the synthesis of semi-synthetic cephalosporins, without any further purification.

The invention is illustrated by the following Examples.

EXAMPLE 1

N-acetoacetylcephalosporin C sodium

Twenty liters of a fermentation broth containing 2860 δ /ml of cephalosporin C were mixed with 800 g of filter aid. Sufficient 30 percent sulphuric acid was added to lower the pH to 2.8. The mixture was filtered, the solids were washed with 8 litres of water, and the washings were combined with the filtrate.

The filtrate was mixed with an equal volume of acetone, and the pH was raised to 8.0 with a sodium hydroxide solution. Whilst keeping the pH of the mixture between 7.8 and 8.2, and its temperature at 5°C, 63.0 g of freshly distilled diketene in 750 ml of acetone were added with stirring. Stirring of the mixture was continued until the pH remained constant, which took about one hour. The acetone was extracted out at neutral pH, using 20 liters of chloroform; and the aqueous phase was acidified to pH 2 with dilute hydrochloric acid (1:1 volume/volume), and extracted with n-butanol.

The butanolic extract was concentrated under reduced pressure, until a viscous residue was obtained. This residue was treated with sodium 2-ethylhexanoate in n-butanol until it had an apparent pH of 4.8. The precipitated product was collected, washed with n-butanol and then with ligroin, and dried under reduced pressure at 40°C, yielding 47 g of the sodium salt of N-acetoacetylcephalosporin C. The product was of adequate purity for use in the preparation of 7-ACA.

For analytical purposes, 1 g of the product was purified by repeated washing with absolute ethanol. The purified product had the following properties:
UV absorption - max. at 259 m$\mu$; min. at 230 m$\mu$.

Rf = 0.68 (Silica gel buffered at pH 5.8. Solvent: 125/25/6.5 methanol/isopropanol/pH 5.8 buffer.) IR (KBr) bands at 1760 cm$^{-1}$ ($\beta$-lactam), 1720 cm$^{-1}$ (acetyl). The sample was not microbiologically active with respect to a cephalosporin C sensitive strain of A. faecalis.

EXAMPLE 2

N-acetoacetylcephalosporin C sodium 500 mg of an authentic sample of cephalosporin C sodium were dissolved in 25 ml of water, and the solution was diluted with 15 ml of acetone. 146 mg of diketene in 10 ml of acetone were added to the solution at 0°C, which was then stirred for 1 hour. The mixture was extracted twice with 50 ml portions of ether, and the aqueous phase was freeze-dried.

The 543 mg of product obtained had the same properties as the product of Example 1.

EXAMPLE 3

Preparation of 7-ACA from N-acetoacetylcephalosporin C sodium 6.3 g of the N-acetoacetylcephalosporin C sodium obtained in Example 2 and 8 ml of quinoline in 72 ml of anhydrous chloroform were reacted with 5.4 ml of dimethyldichlorosilane at room temperature, for 45 minutes, with stirring.

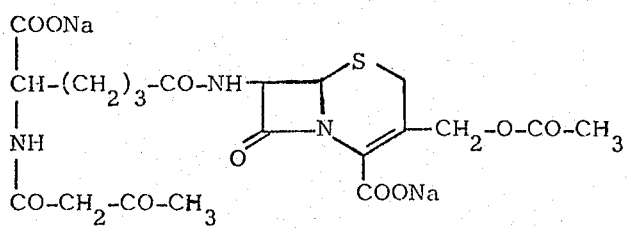

The mixture was then cooled to −22°C, and 4.5 g of phosphorus pentachloride were added. The temperature of the mixture was kept at −22°C for 2 hours. The mixture was then further cooled to −32°C, and 25 ml of propanol was added drop by drop. The temperature rose to −22°C and was maintained at this value for 2 hours. 25 ml of water were then added with stirring. The aqueous phase was separated off; and the organic layer was extracted with a further 20 ml of water. The combined aqueous solution was washed with an equal volume of chloroform, and its pH was raised to 3.5 with ammonium hydroxide.

The aqueous solution was left for 1 hour at 0°C, for the product to crystallize out. The product was collected by filtration, washed with 20 ml of 50 percent methanol, and dried at 45°C under reduced pressure. 2.24 g of 7-ACA were obtained, having a titre of 91 percent as determined by spectrophotometric assay.

EXAMPLE 4

N-acetoacetylcephalosporin C sodium 1200 ml of fermentation broth having an activity corresponding to 25.08 g of cephalosporin C (as determined microbiologically) were diluted with 300 ml of acetone, and the pH was raised to 7.8 – 8.0 with sodium hydroxide solution. The temperature of the mixture was maintained at 5°C while 32 ml of freshly distilled diketene in 80 ml of anhydrous acetone were added with stirring, over a period of ½ hours. The stirring was continued for a further 30 minutes; and during the whole operation the pH was maintained at 7.8 – 8.0 by adding sodium hydroxide solution.

The pH of the reaction mixture was then lowered to 6, the acetone was evaporated off under reduced pressure, and the residue was extracted with 400 ml of methyl isobutyl ketone. The aqueous solution was acidified to pH 2 with cooling, and extracted with 1,200 ml of n-butanol in several portions. The combined butanolic extracts were washed with 100 ml of iced water, dried over $Na_2SO_4$, and concentrated to 500 ml under reduced pressure.

The concentrated extract was treated with 1 N sodium 2-ethylhexanoate in methyl isobutyl ketone until it had an apparent pH of 5. The voluminous precipitate which formed on allowing the solution to stand was collected and dried at 40°C under reduced pressure, yielding 23.73 g of N-acetoacetylcephalosporin C sodium with a purity of 70 percent.

EXAMPLE 5

Preparation of 7-ACA from N-acetoacetylcephalosporin C sodium 4 g of the N-acetoacetylcephalosporin C sodium obtained in Example 4 were suspended in 25 ml of methylene chloride. 1.5 ml of N,N-dimethylanaline, 1.8 ml of triethylamine and, gradually with cooling, 3.1 ml of dimethyldichlorosilane were added to the suspension; and the mixture was maintained at 28° – 30°C, with stirring.

The reaction mixture was then cooled to −60°C. A solution of 6 g of phosphorus pentachloride in 50 ml of methylene chloride was added, followed by 5.5 ml of N,N-dimethylaniline, and the temperature of the mixture was maintained at −40°C for 2 hours. While still keeping the reaction mixture at this same temperature, 30 ml of anhdyrous methanol anhydrous 1.25 ml of N,N-dimethylaniline were added over a period of 15 minutes; and the mixture was then maintained at −40°C for a further 2 hours. 30 ml of warm water were then added with stirring. The aqueous phase was separated off and its pH was raised to 3.8 with ammonium hydroxide.

The resulting suspension was left for 2 hours with cooling, for the product to crystallize out. The product was collected by filtration, washed first with water and then with acetone, and dried at 40°C under reduced pressure. 0.8 g of 7-ACA was obtained, having a titre of 92.3 percent as determined by spectrophotometric assay.

EXAMPLE 6

Preparation of 7-ACA from N-acetoacetylcephalosporin C sodium 4 g of the N-acetoacetylcephalosporin C sodium prepared in Example 1 were transformed into 7-ACA by the same procedure as in Example 5. The resulting 7-ACA had a purity of 92.4 percent as determined by spectrophotometric assay.

EXAMPLE 7

N-dodecanoylcephalosporin C 300 ml of acetone were added to 300 ml of vacuum-concentrated fermentation broth filtrate having a microbiological activity corresponding to 5.12 g of cephalosporin C, and the pH of the mixture was raised to 7.7 with sodium hydroxide solution. A solution of 24 g of dodecanoyl chloride in 50 ml of acetone was added with stirring, over a period of 3 hours, at a temperature of 30°C and while maintaining the pH of the mixture at 7.7 by addition of sodium hydroxide solution. The mixture was allowed to react for a further hour at pH 7.0, then the acetone was evaporated off under reduced pressure and the excess dodecanoic acid was filtered off.

100 ml of benzene were added to the filtrate and the aqueous phase was acidified to pH 2.0 with 5 N hydrochloric acid. The benzene layer was separated off, and the aqueous phase was extracted with a second 100 ml portion of benzene. The benzene extracts were combined and kept overnight at a temperature of 7°C. The precipitate which formed was filtered off and dried under reduced pressure, yielding 5.3 g of N-dodecanoylcephalosporin C having a potentiometric titre of 97.5 percent. Yield 80 percent.

The product was subjected to thin-layer chromatography. (Silica gel "GF 254" buffered with phosphate buffer at pH 5.8.Solvent: methanol/isopropanol/phosphate buffer pH 5.8: 125/25/6.5. Indicator: iodine/-$NaN_3$. Temperature: 110°C). It gave a white spot at Rf = 0.70, m.p. 132° = 134°C.

UV spectrum: $\lambda_{max.} = 260$ m$\mu$; $\lambda_{min.} = 233$ m$\mu$. $E_{1\,cm}^{1\,percent} = 110$ in 0.1N $NaHCO_3$ solution at 260 m$\mu$. IR spectrum: 3270, 2920, 2850, 1755, 1725, 1645, 1530, 1380, 1235, 1032 cm$^{-1}$.

EXAMPLE 8

Preparation of 7-ACA from N-dodecanoylcephalosporin C 3.6 g of the N-dodecanoylcephalosporin C prepared in Example 7 were suspended in 25 ml of methylene chloride, and 2.55 ml of triethylamine and 1.92 ml of N,N-dimethylaniline were added to the suspension. The mixture was cooled to 5°C, 2.85 ml of dimethyldichlorosilane were slowly added, and the reaction mixture was then stirred for 2 hours at 28°C.

The reaction mixture was cooled to −60°C, and a solution of 3.75 g of phosphorus pentachloride in 30 ml of methylene chloride was added, followed by 3 ml of N,N-dimethylaniline. The mixture was stirred for 2 hours at −40°C; the temperature was again lowered to −60°C, and 20 ml of methanol containing 0.4 ml of N,N-dimethylaniline were slowly added; and the mixture was then again stirred for 2 hours at −40°C.

20 ml of warm water were added to the reaction mixture, the aqueous phase was separated off, and the organic layer was extracted with 10 ml of water. The aqueous extracts were combined, the pH adjusted to 3.7 with ammonium hydroxide, and the resulting solution was left overnight under cooling. The precipitate which formed was collected by filtration, washed with water and acetone, and dried under reduced pressure, yielding 1.20 g of 7-ACA having a titre of 90.2 percent (as determined by UV spectrophotometry). Yield 67.5 percent.

EXAMPLE 9

N-dodecanoylcephalosporin C monosodium salt 2600 ml of filtered fermentation broth with a cephalosporin C activity of 2750 δ/ml were treated with an equal volume of acetone. The precipitate which formed was filtered off, and the pH of the filtrate was raised to 7.8 with sodium hydroxide solution.

48.2 g of dodecanoyl chloride were then added to the filtrate over a period of 3 hours, with vigorous stirring, while keeping the filtrate at 30°C and maintaining its pH at 7.8 by addition of sodium hydroxide solution. After half an hour, the pH was lowered to 7.0, the acetone was evaporated off under reduced pressure, and the dodecanoic acid was removed by filtration. The solution was acidified to pH 6.0 with 5 N hydrochloric acid and extracted with 200 ml of benzene, to eliminate residual dodecanoic acid.

The resulting solution was then acidified to pH 2.0 with 5 N hydrochloric acid, and extracted with 300 ml of ethyl acetate in four portions. The combined organic extracts were washed with 100 ml of iced water, dried over anhydrous sodium sulphate, and concentrated to 100 ml at 25°C under reduced pressure. The concentrate was treated with 1 N sodium 2-ethylhexanoate in methyl isobutyl ketone to an apparent pH of 5.5, then left to stand under cooling. The precipitate which formed was collected by filtration and dried under reduced pressure, yielding 5.4 g of the monosodium salt of N-dodecanoylcephalosporin C. The product had the same chromatographic and spectrophotometric characteristics as the product of Example 7.

EXAMPLE 10

Preparation of 7-ACA from N-dodecanoylcephalosporin C monosodium salt 1.2 g of the monosodium salt of N-dodecanoylcephalosporin C prepared in Example 9 were subjected to the procedure of Example 8, yielding 0.27 g of 7-ACA having a titre of 88.5 percent, as determined by spectrophotometric assay.

We claim:

1. In a process of recovering cephalosporin C from a fermentation broth thereof by treating said broth with a reactant which causes a protecting moiety to become attached to the amino side chain of said cephalosporin C, the improvement which comprises employing an acid chloride of the formula R-CO-Cl, wherein R is an aliphatic hydrocarbon radical of 9–21 carbon atoms, as said reactant and wherein said fermentation broth is treated with at least 1.5 mols of said reactant per mol of cephalosporin C in the broth.

2. The process of claim 1 wherein said fermentation broth is treated with from 2–15 mols of said reactant per mol of cephalosporin C in the broth, at a pH of about 8, while maintaining the temperature of the broth in the range of from −10° C. to +40° C.

3. The process of claim 1 wherein said reactant is selected from the group consisting of decanoyl chloride, dodecanoyl chloride and hendecenoyl chloride.

4. In the process of recovering cephalosporin C from a fermentation broth thereof by treating said broth with a reactant which causes a protecting moiety to become attached to the amino side chain of said cephalosporin C and thereafter recovering the resulting protected cephalosporin C from said broth by extraction with a water immiscible organic solvent at an acid pH, the improvement which comprises employing an acid chloride of the formula R-CO-Cl, wherein R is an aliphatic hydrocarbon radical of 9–21 carbon atoms, as said reactant.

5. The process of claim 4 wherein said reactant is selected from the group consisting of decanoyl chloride, dodecanoyl chloride, and hendecenoyl chloride.

6. In the process of preparing 7-aminocephalosporanic acid which comprises the steps of treating a cephalosporin C fermentation broth with a reactant which causes a protecting moiety to become attached to the amino side chain of said cephalosporin C, recovering the resulting protected cephalosporin C from said broth by extraction with a water immiscible organic solvent at acid pH, forming a silyl di-ester of said protected cephalosporin C, halogenating said silyl di-ester thereby forming the corresponding imino-halide, reacting said imino-halide with a lower aliphatic alcohol thereby forming the corresponding imino-ether, and hydrolyzing said imino-ether under acidic conditions thereby forming the desired 7-aminocephalosporanic acid, the improvement which comprises employing and an acid chloride of the formula R-CO-Cl, wherein R is an aliphatic hydrocarbon radical of 9–21 carbon atoms, as said reactant.

7. The process of claim 6 wherein said reactant is selected from the group consisting of decanoyl chloride, dodecanoyl chloride and hendecenoyl chloride.

8. In the process of preparing 7-aminocephalosporanic acid which comprises the steps of forming a silyl di-ester of an amino side chain protected cephalosporin C, halogenating said silyl di-ester thereby forming the corresponding imino-halide, reacting said imino-halide with a lower aliphatic alcohol thereby forming the corresponding aminoether, and hydrolyzing said iminoether under acidic conditions thereby forming the desired 7-aminocephalosporanic acid, the improvement which comprises employing as said amino side chain protected cephalosporin C, a compound of the formula

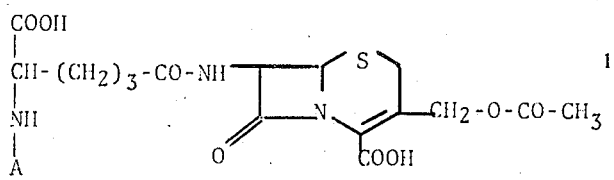

wherein A is selected from the group consisting of CH₃COCH₂CO and R-CO-, wherein R is a hydrocarbon radical of 9–21 carbon atoms.

9. The process of claim 8 wherein said amino side chain protected cephalosporin C is selected from the group consisting of N-decanoylcephalosporin C, N-dodecanoylcephalosporin C, and N-hendecenoylcephalosporin C.

10. A cephalosporin derivative of the formula

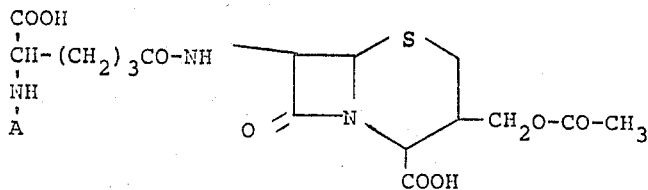

wherein A is R-CO-, R representing an aliphatic hydrocarbon group of 9–21 carbon atoms; the sodium, potassium, calcium, zinc, iron, cadmium, copper, aluminum, ammonium, and organic base salts thereof, wherein said organic base is selected from the group consisting of quinoline, cyclohexylamine, 5-ethyl-2-methylpyridine, 2-picoline, 3-picoline, 4-picoline, N-ethylmorpholine, N-methylmorpholine, 2,6-lutidine, N,N-diethylcyclohexylamine, hexamethylenetetramine, N,N-diethylbenzylamine, and N,N-dibenzylethylenediamine.

11. The cephalosporin derivative of claim 10 wherein the compound of said formula is selected from the group consisting of N-decanoylcephalosporin C, N-dodecanoylcephalosporin C, and N-hendecenoylcephalosporin C.

* * * * *